US008290565B2

(12) United States Patent
Ehman et al.

(10) Patent No.: US 8,290,565 B2
(45) Date of Patent: Oct. 16, 2012

(54) SYSTEM AND METHOD FOR CYCLIC MOTION ENCODING FOR ENHANCED VISUALIZATION OF SLIP INTERFACES WITH MRI

(75) Inventors: Richard L. Ehman, Rochester, MN (US); Yogesh K. Mariappan, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 372 days.

(21) Appl. No.: 12/418,109

(22) Filed: Apr. 3, 2009

(65) Prior Publication Data

US 2009/0253979 A1 Oct. 8, 2009

Related U.S. Application Data

(60) Provisional application No. 61/042,437, filed on Apr. 4, 2008.

(51) Int. Cl.
*A61B 5/05* (2006.01)
(52) U.S. Cl. .................. 600/410; 600/411; 600/421
(58) Field of Classification Search .............. 600/407, 600/410, 411, 437, 442, 443; 383/128, 130
See application file for complete search history.

(56) References Cited

U.S. PATENT DOCUMENTS

| 5,825,186 | A | 10/1998 | Ehman et al. | |
|---|---|---|---|---|
| 6,647,134 | B1* | 11/2003 | McGee et al. | 382/128 |
| 6,862,468 | B2* | 3/2005 | Smith | 600/410 |
| 7,025,253 | B2* | 4/2006 | Sinkus et al. | 324/309 |
| 2006/0253020 | A1* | 11/2006 | Ehman et al. | 600/411 |
| 2006/0264736 | A1* | 11/2006 | Ehman et al. | 600/410 |
| 2007/0100246 | A1* | 5/2007 | Hyde | 600/509 |
| 2007/0145975 | A1* | 6/2007 | Feiweier et al. | 324/307 |

OTHER PUBLICATIONS

S Papazoglou et al; Horizontal Shear Wave Scattering From a Nonwelded Interface Observed by Magnetic Resonance Elastography; Physics in Medicine and Biology 52 (2007)675-684.
Andreas Lienemann et al; Detection and Mapping of Intraabdominal Adhesions by Using Functional Cine MR Imaging: Preliminary Results; Radiology, Nov. 2000,vol. 217, No. 2; pp. 421-425.
Kevin J. Glaser et al; Shear Stiffness Estimation Using Intravoxel Phase Dispersion in Magnetic Resonance Elastography; Magnetic Resonance in Medicine 50:1256-1265 (2003).
R Muthupillai et al; Magnetic Resonance Elastography by Direct Visualization of Propagating Acoustic Strain Waves; Science, vol. 269 Sep. 20, 1995, http://www.jstor.org; Mon Mar 10 12:02:59 2008.
Yin, Meng, et al., Assessment of Hepatic Fibrosis with Magnetic Resonance Elastography, Clinical Gastroenterology and Hepatology 2007; 5:1207-1213.

* cited by examiner

*Primary Examiner* — James Kish
*Assistant Examiner* — Michael N Fisher
(74) *Attorney, Agent, or Firm* — Quarles & Brady, LLP

(57) ABSTRACT

A system and method for producing an image of a functional tissue slip interface using MRI. The method includes applying an external stimulus to a subject to impart relative shearing motion at a tissue interface. NMR signals are then acquired from a ROI including the slip interface using a motion encoding gradient to sensitize the acquired NMR signals to the shearing motion. MR images indicative of the degree of mechanical shear connectivity at the tissue interface are reconstructed from the acquired NMR signals in which low-friction shearing motion at the tissue interface is characterized by a loss of magnitude signal due to intravoxel phase dispersion.

20 Claims, 5 Drawing Sheets

402

$\alpha N$ $M_1$ $\theta_1$ $M_1 e^{i\theta_1}$ — 406

404

$(1-\alpha)N$ $M_2$ $\theta_2$ $M_2 e^{i\theta_2}$

FIG. 4

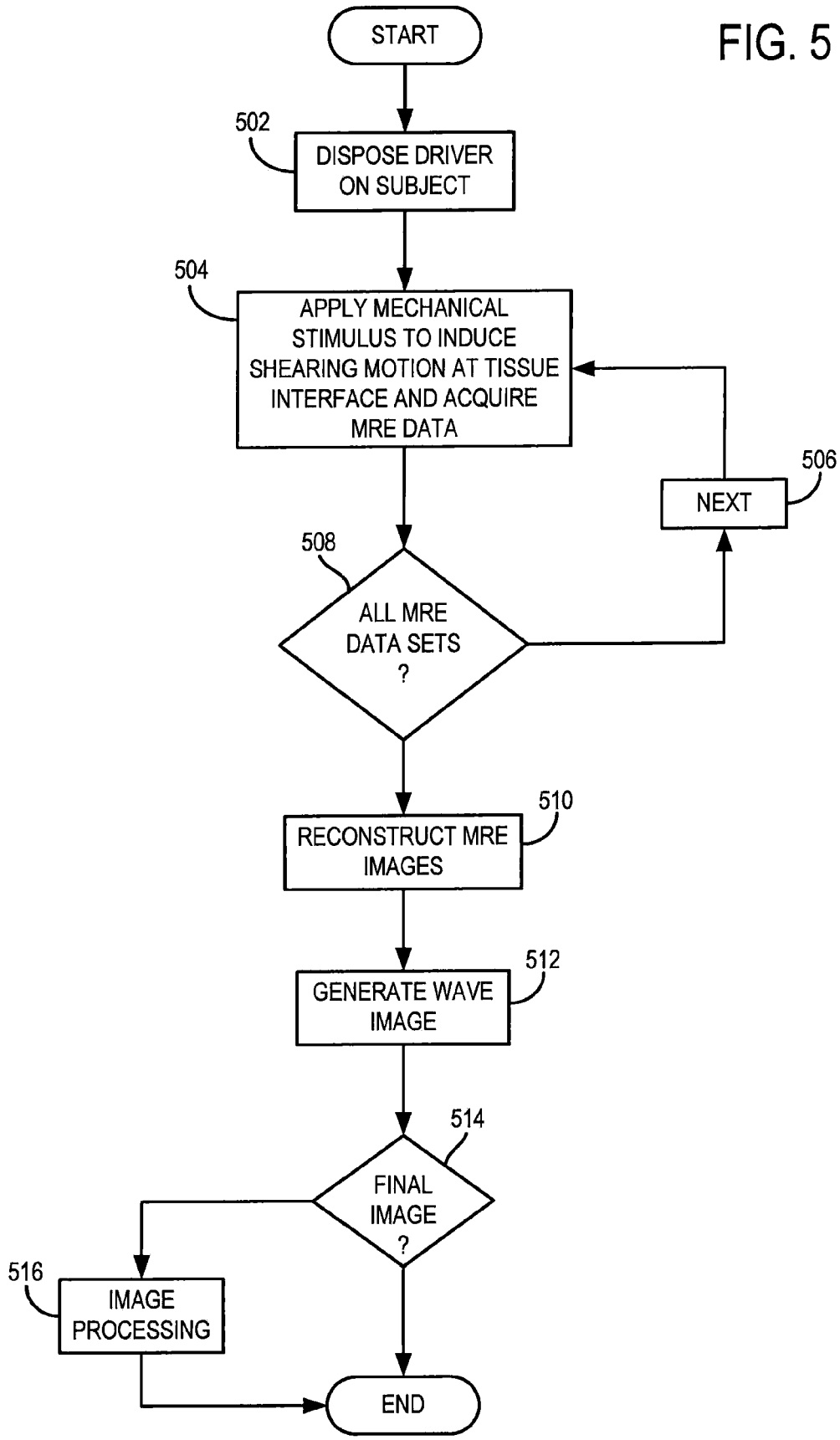

SYSTEM AND METHOD FOR CYCLIC MOTION ENCODING FOR ENHANCED VISUALIZATION OF SLIP INTERFACES WITH MRI

CROSS REFERENCE TO RELATED APPLICATIONS

This application claims the benefit of U.S. Provisional Application 61/042,437, filed Apr. 4, 2008, which is incorporated herein in its entirety for all purposes.

STATEMENT REGARDING FEDERALLY SPONSORED RESEARCH

This invention was made with government support under Grant No. NIH EB001981. The United States Government has certain rights in this invention.

FIELD OF THE INVENTION

The present invention relates to a system and methods for assessing mechanical shear connectivity across tissue interfaces.

BACKGROUND

The presence of low-friction interfaces allowing shearing motion between tissue surfaces is critical for the normal function of many structures in the body. Biological evolution has provided several solutions for this requirement. Apposed serosal surfaces in the pleura, pericardium, and peritoneum provide a slip interface needed for the normal function of the lungs, heart, and intra-abdominal organs, respectively. Bursal structures allow the shearing motions necessary for function of tendons and parts of the musculoskeletal system. Areolar adipose tissue surrounding blood vessels, muscles, and the capsules of organs provides for smaller degrees of shear motion, allowing relative movement between structures during gross body motion and breathing.

The loss of functional shear interfaces, such as due to scarring or tumor invasion, can lead to serious consequences. For instance, the development of adhesions between the visceral and parietal peritoneum in the abdomen, typically due to scarring following surgery, can lead to functional impairment, intermittent bowel obstruction or acute conditions with catastrophic ischemic consequences. Adhesions in peritendinous tissues can cause serious impairment in extremity and hand function. The loss of normal areolar tissue around the carotid arteries following radiotherapy, and its subsequent replacement with fibrosis, subjects these structures to increased mechanical stress during normal body motion, which is thought to be instrumental in the accelerated development of atherosclerotic changes in these patients.

Conventional imaging techniques such as MRI and CT can depict the gross morphology of tissues at structural shear interfaces and may demonstrate focal thickening or other changes that are likely to be associated with loss of slip functionality. However, they do not directly assess the slip functionality at tissue interfaces.

An imaging technique called MR Elastography (MRE) that can measure the elasticity of tissues has been introduced as disclosed in U.S. Pat. No. 5,592,085. Oscillatory stresses are applied to tissues-of-interest and tissue displacement due to the resulting propagation of shear waves is imaged by encoding the motion into the phase of the MR signals. From images reconstructed from these MR signals, the mechanical properties of the subject can be determined. In many applications, the production of shear waves in the tissues is merely a matter of physically vibrating the surface of the subject with an electromechanical device such as that disclosed in U.S. Pat. No. 5,952,828 or by an acoustic driver such as that described in co-pending U.S. patent application Ser. No. 10/860,174 filed on Jun. 3, 2004.

While the above-discussed method allows the mechanical properties of tissues to be imaged, it does not currently allow the degree of connectivity at tissue slip interfaces to be analyzed. Specifically, it cannot distinguish between functional shearing interfaces and damaged shearing interfaces in which shearing motion between two opposing tissues is at least partially impeded. There is evidence that MRE-based techniques may be used to assess the weldedness of tissue interfaces, as proposed by Papazoglou, et al., in "Horizontal shear wave scattering from a nonwelded interface observed by magnetic resonance elastography." Phys. Med. Biol. 2007; 52:675-684. However, this is an indirect method that uses a complicated mathematical algorithm to model the scattering of shear waves at tissue interfaces.

It would therefore be desirable to have a simple and direct method for sensitively assessing mechanical shear connectivity across tissue interfaces, which would allow for the identification of damaged tissue interfaces.

SUMMARY OF THE INVENTION

The present invention overcomes the aforementioned drawbacks by providing a method for analyzing the degree of mechanical shear connectivity at tissue slip interfaces. The method includes employing MRE techniques to acquire MR images in which shearing motion at a slip interface is characterized by a reduced magnitude signal due to the effects of intravoxel phase dispersion. This method can depict functional shearing interfaces directly in an MR magnitude image and does not require complicated modeling and analysis of shear wave propagation and scattering at tissue interfaces.

The present invention provides a method for producing an image indicating an integrity of a tissue interface in a subject with a magnetic resonance imaging (MRI) system. The method includes applying an oscillatory stress to the subject to impart a relative shearing motion between tissues at opposing sides of a common tissue interface and acquiring NMR signals from a region-of-interest including the tissue interface with the MRI system, while applying a motion encoding gradient along the direction of the imparted relative shearing motion to sensitize the acquired NMR signals to the relative shearing motion at the tissue interface. The method also includes reconstructing at least one MRE image from the acquired NMR signals, analyzing the at least one reconstructed MRE image to determine a loss of signal intensity due to intra-voxel phase dispersion resulting from the imparted relative shearing motion at the tissue interface, and producing, from the determined loss of signal intensity, an image indicative of the mechanical connectivity between the tissues at opposing sides of the common tissue interface.

In an alternative embodiment the present invention provides a method of producing an image of a tissue interface in a subject using a magnetic resonance imaging (MRI) system. The method includes applying an oscillatory stimulus to the subject to impart relative shearing motion between tissues at opposing sides of a common tissue interface and acquiring NMR signals from a region-of-interest including the tissue interface, while applying a motion encoding gradient along the direction of the relative shearing motion to sensitize the acquired NMR signals to the relative shearing motion between the tissues. An MRE image indicating a degree of mechanical shear connectivity at the tissue interface is then reconstructed from the acquired NMR signals.

Various other features of the present invention will be made apparent from the following detailed description and the drawings.

BRIEF DESCRIPTION OF THE DRAWINGS

FIG. 4 depicts a two-compartmental model used to characterize signal loss due to intra-voxel phase dispersion in accordance with the present invention; and FIG. 5 is a flowchart setting forth the steps for producing a MR image of a tissue slip interface in accordance with the present invention.

DESCRIPTION OF THE PREFERRED EMBODIMENT

Figure 1:
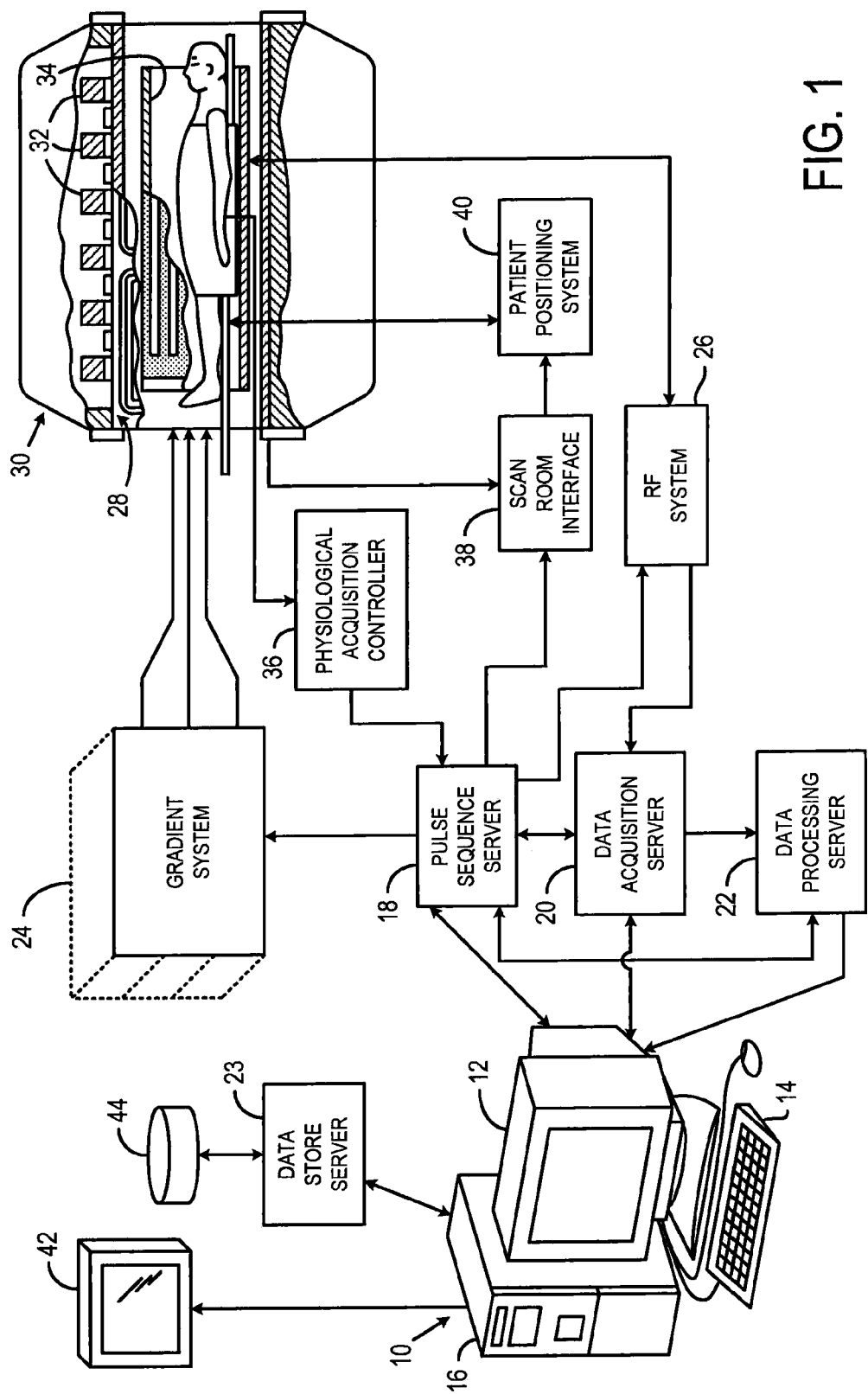
FIG. 1 is a block diagram of an MRI system that employs the present invention.

Referring first to FIG. 1, the preferred embodiment of the invention is employed in an MRI system. The MRI system includes a workstation 10 having a display 12 and a keyboard 14. The workstation 10 includes a processor 16 which is a commercially available programmable machine running a commercially available operating system. The workstation 10 provides the operator interface which enables scan prescriptions to be entered into the MRI system.

The workstation 10 is coupled to four servers: a pulse sequence server 18; a data acquisition server 20; a data processing server 22, and a data store server 23. In the preferred embodiment the data store server 23 is performed by the workstation processor 16 and associated disc drive interface circuitry. The remaining three servers 18, 20 and 22 are performed by separate processors mounted in a single enclosure and interconnected using a 64-bit backplane bus. The pulse sequence server 18 employs a commercially available microprocessor and a commercially available quad communication controller. The data acquisition server 20 and data processing server 22 both employ the same commercially available microprocessor and the data processing server 22 further includes one or more array processors based on commercially available parallel vector processors.

The workstation 10 and each processor for the servers 18, 20 and 22 are connected to a serial communications network. This serial network conveys data that is downloaded to the servers 18, 20 and 22 from the workstation 10 and it conveys tag data that is communicated between the servers and between the workstation and the servers. In addition, a high speed data link is provided between the data processing server 22 and the workstation 10 in order to convey image data to the data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and $G_z$ used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2+Q^2},$$

and the phase of the received NMR signal may also be determined:

$$\phi=\tan^{-1} Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

It should be apparent that the pulse sequence server 18 performs real-time control of MRI system elements during a scan. As a result, it is necessary that its hardware elements be operated with program instructions that are executed in a timely manner by run-time programs. The description components for a scan prescription are downloaded from the workstation 10 in the form of objects. The pulse sequence server 18 contains programs which receive these objects and converts them to objects that are employed by the run-time programs.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with description components downloaded from the workstation 10. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 2:
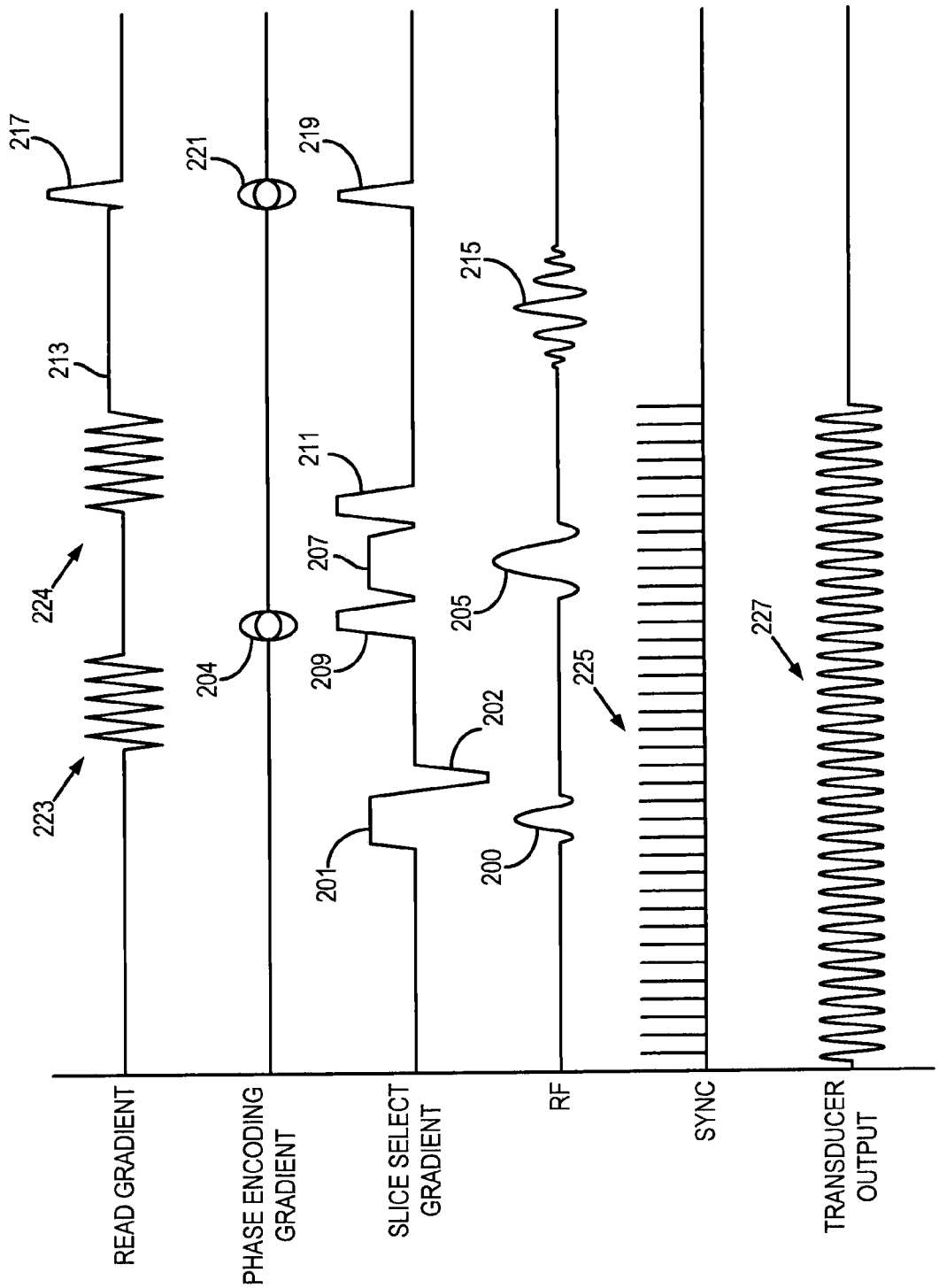
FIG. 2 is a MRE pulse sequence in accordance with the present invention.

Referring to FIG. 2, a pulse sequence for acquiring MRE data in accordance with the present invention is shown. The pulse sequence is fundamentally a 2DFT pulse sequence using a spin-echo. Transverse excitation is produced by a 90 degree RF excitation pulse 200 in the presence of a slice-select gradient ($G_z$) pulse 201 followed by a rephasing lobe 202, which mitigates signal loss resultant from phase dispersions introduced by the slice selection gradient 201. A phase encoding gradient ($G_y$) pulse 204 is applied at an amplitude and polarity determined by the view number of the acquisition. A 180 degree RF refocusing pulse 205 is then applied in the presence of slice-selection gradient 207. To substantially reduce unwanted phase dispersions, a first crusher gradient 209 bridges the slice selective gradient 207 with a second crusher gradient 211. A positive readout gradient pulse 213 is applied and an NMR signal 215 is acquired to frequency encode digitized samples. The pulse sequence concludes with spoiler gradient pulses 217 and 219 along the read and slice select axes and a rephasing pulse 221 along the phase encoding axis.

To practice the present invention an alternating magnetic field gradient is applied after the transverse magnetization is produced and before the NMR signal is acquired. In the embodiment illustrated in FIG. 2, the read gradient ($G_x$) is used for this function and is alternated in polarity to produce a first set of bipolar gradient waveforms 223 before the application of the 180 degree refocusing pulse 205, and a second set of bipolar gradient waveforms 224 after the application of the 180 degree refocusing pulse 205. These gradient waveforms are referred to as motion-encoding gradient (MEG) waveforms. The second set of MEG waveforms 224 are played out 180 degrees out of phase with the first set of bipolar gradient waveforms 223 so that phase is properly accumulated. Typically, 1-10 cycles of these MEG waveforms with frequencies ranging from 50 to 200 Hz are included in the pulse sequence, depending upon the clinical application. At the same time, the pulse sequence server 18 produces sync pulses as shown at 225, which are at the same frequency and have a specific phase relationship with the alternating gradient pulses 223 and 224. As will be explained below, these sync pulses 225 activate a transducer to apply an oscillating stress 227 to the patient, which generally has the same frequency and phase relationship as the MEG. To ensure that the resulting waves have time to propagate throughout the field of view, the sync pulses 225 may be turned on well before the pulse sequence begins, as is shown in FIG. 2.

The phase of the NMR signal 215 is indicative of the movement of the spins. If the spins are stationary, the phase of the NMR signal is not altered by the MEG pulses 223 and 224, whereas spins moving along the direction of the motion encoding gradient will accumulate a phase proportional to their displacement. Spins which move in synchronism and in phase with the alternating magnetic field gradients 223 and 224 will accumulate maximum phase of one polarity, and those which move in synchronism, but 180 degrees out of phase with the alternating magnetic field gradients 223 and 224 will accumulate maximum phase of the opposite polarity. The phase of the acquired NMR signal 215 is thus affected by the "synchronous" movement of spins along the motion encoded direction.

The pulse sequence in FIG. 2 can be modified to measure synchronous spin movement along the other gradient axes. For example, the MEG pulses may be applied along the phase encoding axis or they may be applied along the slice select axis. Indeed, they may be applied simultaneously to two or three of the gradient field directions to "read" synchronous spin movements along any desired direction.

Figure 3:
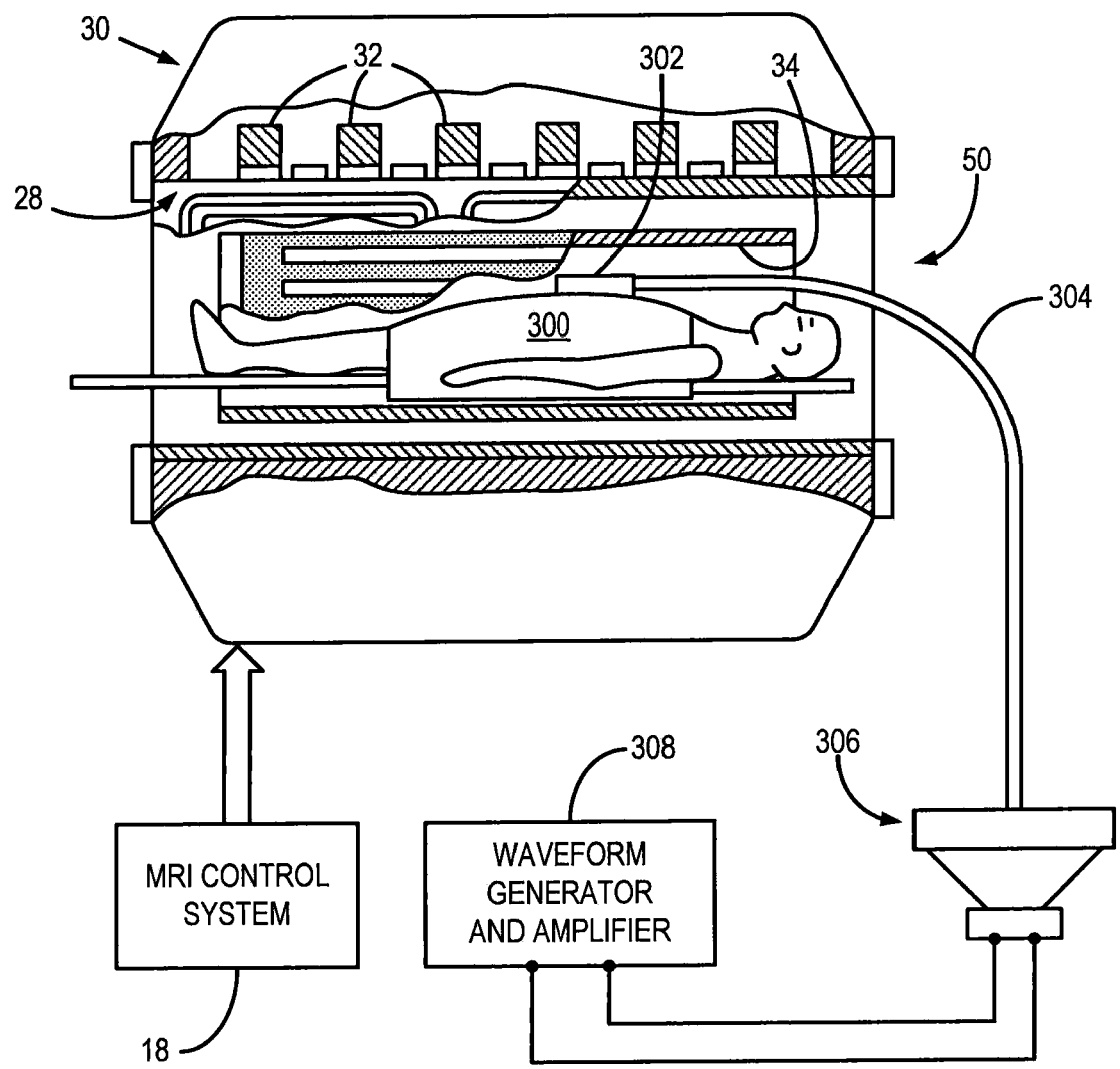
FIG. 3 depicts a MRE acoustic driver system in accordance with the present invention.

Referring particularly to FIG. 3, a subject to be examined 300 is placed in the bore of the MRI system magnet 30 and is subjected to magnetic fields produced under the direction of a selected pulse sequence. An MRE acoustic driver such as that described in co-pending U.S. patent application Ser. No. 10/860,174 filed on Jun. 3, 2004 and entitled "Pressure Activated Driver For MR Elastography" is used to apply an oscillating stress to the subject's liver. It includes a passive actuator 302 which is positioned over the region of interest in the subject 300 and is connected by means of a tube 304 to a remotely located driver assembly 306. The driver assembly 306 is remote from the magnet 30 in the sense that it is away from the strong magnetic fields produced by the magnet 32 where its operation is not impeded by those fields, and where its operation will not perturb the MRI system magnetic fields. The driver assembly 306 is electrically driven by a waveform generator and amplifier 308, which in turn is controlled by the pulse sequence server 18.

The pulse sequence server 18 directs the MRI system to perform the above-described MRE pulse sequence, and in doing so it outputs the synchronizing pulses 225 to the waveform generator and amplifier 308. As described in the above-cited co-pending application, the sync pulses 225 enable the waveform generator 308 to produce an oscillatory signal at the proper moment during each MRE pulse sequence. This signal energizes a loudspeaker in the active driver 306 to produce acoustic waves that are coupled to the passive driver 302 through tube 304. The passive driver 302 has a membrane that is vibrated by this acoustic wave to stress tissues against which it bears.

Intravoxel phase dispersion (IVPD) is a phenomenon in which the magnitude signal of an image volume element, a voxel, is reduced due to the presence of significant phase variations within the voxel. This occurs because the magnitude signal of a voxel is a vector sum of the magnetization of the isochromats (spins) it contains. IVPD can occur in traditional MR images, but is viewed as an undesirable image artifact that may be corrected. For example, phase variations in the slice-selection direction as well as the in-plane directions can cause IVPD.

The present invention may employ the above-described MRE system and pulse sequence to exploit IVPD effects by purposely introducing shear waves into the body and mapping the motion of tissues on either side of a tissue slip interface into the phase of MR images. This can produce phase discontinuities in the MR data indicative of the degree of connectivity of mechanical shear interfaces, effectively providing contrast between low-friction slip interfaces (typically healthy) and high-friction slip interfaces (typically less healthy).

Referring now to FIG. 4, a two-compartmental model may be used to relate the amount of magnitude signal reduction in a given voxel to phase difference across the interface voxel. A schematic representation of a two-compartmental model for an interface voxel having a top compartment 402 having spins moving in a particular way and a bottom compartment 404 with spins moving in a different way, on opposing sides of a tissue interface 406 is provided in FIG. 4a. The total number of spins in the voxel and the fraction of spins in the top compartment of the voxel are respectively denoted as N and $\alpha$, implying that the top compartment 402 has $\alpha$N spins and the bottom compartment 404 has $(1-\alpha)$N spins. FIG. 4 depicts the situation with $\alpha$ equal to 0.50, that is, the interface is exactly in the middle of the voxel. The magnitudes of the isochromats in the top and bottom compartments are respectively denoted as $M_1$ and $M_2$ and the corresponding phases are denoted as $\theta_1$ and $\theta_2$. In this case it is assumed that the magnitude of the isochromats of both the compartments is the same with unit value. The spins in each compartment have the same compartment specific phase. The phase of the spins is dependent upon the amount of displacement, for example, displacement due to shearing motion of two tissues at an interface, and the properties of the motion-encoding gradients of the MRE pulse sequence used. The net magnitude signal of this model voxel (R) is therefore the vector sum of all the spins in the two compartments and is given by:

$$\frac{R^2}{N^2} = 1 - 4\alpha(1-\alpha)\sin^2\left(\frac{\Delta\theta}{2}\right);\quad\text{Eqn. 1}$$

where $\Delta\theta$ is the phase difference across the voxel, which is calculated as $(\theta_1-\theta_2)$. With this model, the total number of spins present in a voxel is only a scaling factor for the absolute magnitude value and the relative magnitude signal loss is only dependent upon the phase difference between the two compartments and the fraction of spins present in each compartment. If $\Delta\theta$ is zero, then $R^2/N^2=1$, implying that there is no signal loss due to shear motion in the voxel. The magnitude signal is lowest when the phase difference is $\pi$ for any particular value of $\alpha$, going to zero when $\alpha$ is 0.5. The magnitude signal reaches its lowest relative value when the interface is exactly in the middle of the voxel ($\alpha=0.5$) and the equation reduces to:

$$\frac{R^2}{N^2} = \cos^2\left(\frac{\Delta\theta}{2}\right)\quad\text{Eqn. 2}$$

where the MR signal at a given interface voxel has a $\sin^2$ dependence on the phase difference across the interface. If sinusoidal motion of a particular frequency is introduced, then the magnitude signal variations over time occur at twice this frequency due to the temporal behavior of the phase difference and because $\sin^2(\Delta\theta)$ is an even function.

Referring particularly to FIG. 5, a method for imaging a tissue slip interface begins at process block 502 with the placement of an MRE acoustic driver on a subject within the bore of an MRI system. The location and orientation of the driver are selected so that, when activated, the driver will cause relative shearing motion between two tissues on opposing sides of a common tissue interface. For example, when detecting the interfaces between the functional compartments of the multi-tendoned forearm flexor muscles, the flexor digitorum profundus and the flexor digitorum superficialis, a small passive driver may be placed on an individual finger to allow the production of vibrations that propagate up the forearm and cause shear motion at the tissue interface.

At process block 504 a first MRE data acquisition stage begins under the operation of an MRE pulse sequence like that of FIG. 2. During this acquisition stage, the driver is activated to impart shearing motion between two tissues on opposing sides of a tissue interface being studied. The MRE pulse sequence may include two cyclic motion-encoding gradient (MEG) waveforms on either side of 180 degree RF pulse to sensitize the acquisition to motion in the direction of the shearing motion at the tissue interface. Further, the amplitude of the MEG waveforms may be increased over the acquisition to encode an increasing amount of phase into the motion at the tissue interface. Following the acquisition of NMR data, the system proceeds to a second MRE data acquisition stage at process block 506. This acquisition stage is similar to the first, but the motion-encoding gradients are altered to cause a phase opposition between NMR data acquired in the first and second acquisition stages. For example, the polarities of the MEG waveforms in the second acquisition stage may be inverted relative to those of the first acquisition stage. The acquired first and second MRE data sets may be considered to constitute a MRE data set pair.

More MRE data set pairs may be acquired in the same manner until, at decision block 508, it is determined that a sufficient amount of MRE data sets have been acquired. For example, MRE data set pairs at four to eight temporal positions within a single wave cycle may be acquired to produce a time-series of images showing tissue interface slip functionality at different stages of tissue displacement. At process block 510, pairs of MRE images are created by reconstructing the acquired MRE data set pairs. For example, complex, two-dimensional Fourier transformation may be employed to reconstruct a first and second MRE image from the first and second MRE data sets. At process block 512, a complex MRE wave image is produced from these MRE image pairs by taking the mean of the magnitudes of the two images and calculating the difference of the phases of the two data sets. For example, an MRE wave image may be produced by taking the geometric mean and phase difference for corresponding pixels of the first and second MRE images. These MR wave images contain magnitude signal loss at the tissue interface indicative of IVPD resultant from the imparted shearing motion at the tissue interface. Therefore, a magnitude image obtained directly from the wave image can be analyzed to identify tissue slip boundaries.

While the produced wave images show signal loss at tissue interfaces, it can sometimes be difficult to discern between signal loss to IVPD and inherent MR image contrast between two different tissues. Accordingly, at decision block 514, it may be determined that additional image processing steps will be applied to accentuate or clarify the tissue interface, as indicated at process block 516. For example, a pseudo-magnitude filter analysis may be performed by creating a complex image with unit magnitude and with phase equal to that of the wave image. Signal loss can then be produced by low-pass filtering the complex image, for example, by employing a nine-point Hamming-windowed low-pass filter with a normalized cutoff frequency of 0.5.

Alternately, two-dimensional phase difference images may be calculated by root-sum-of-squares from the one-dimensional phase difference values in the x-direction and y-direction of the phase of the MRE wave image, since tissue interfaces generally not depicted with a single dimension. Relative magnitude signal estimates may then be calculated from these values using Eqn. 1 and by assuming that $\alpha$ is equal to 0.5. These estimates represent the maximum observable magnitude loss at an interface voxel for generally obliquely oriented interfaces of surrounding voxels where the phase differences are entirely due to slip interface motion. This approach to maximize the contrast at tissue slip interfaces due to the assumed $\alpha$ value of 0.5 is advantageous because it avoids the intrinsic MR imaging contrast between different tissues. This approach utilizes information from voxels neighboring the central tissue interface voxel and assumes that the phase differences across the neighboring voxels are entirely due to the slip interface in the central voxel. By contrast, shear lines in magnitude images obtained directly from wave images are due to phase variations within the central voxel itself.

This method can, for example, be used to detect the slip interface present between the small bowel and the abdominal peritonal wall, where the loss of the slip interface due to the formation of adhesions following abdominal surgeries is a significant problem. To create relative motion between these two tissues, a MRE acoustic driver may be placed on the abdomen of the subject being imaged. Axial MRE images of the subject may then be obtained with the subject disposed in the prone position while applying longitudinal motion at 90 Hz to the abdomen in the anterior-posterior direction and encoding motion in this direction into the wave images. Additional imaging parameters may include a 32 cm FOV, a 256× 64 acquisition matrix, 33.3 ms TR, 19.2 ms TE, 30 degree flip angle, 16 kHz receiver bandwidth, 5 mm slice thickness, right-left frequency encoding direction, and 4 time offsets acquired during a single breath-hold using parallel imaging with an 8-channel torso array coil. Images produced using the above settings may include magnitude signal loss due to IVPD and intrinsic MR contrast between tissues. Therefore, to identify the signal due to IVPD resulting from relative shearing motion at the interface, a pseudo-magnitude filter analysis using the above-described Hamming filter may be performed. Alternately, differentiation of signal loss due to IVPD from inherent MR signal contrast may also be provided by the above-discussed two-dimensional phase difference method.

It is contemplated that the present invention may be employed to detect abdominal adhesions, which cause chronic pain, bowel obstruction, and infertility. At the location of an adhesion, the slipperiness of the tissue interface is lost, resulting in mechanical coupling of tissues on either side of the interface. Therefore, vibrations introduced into the body in accordance with the present invention would propagate across the adhesion-affected tissue interface and cause the tissues on either side of the interface to vibrate in synchrony. As a result, there would be no phase discontinuities across the tissue interface and the loss of tissue interface slip functionality would be characterized by the absence of shear lines in MR images acquired according to the present invention. CINE MRI and ultrasound are currently being investigated for the detection of abdominal adhesions. However, because MRE pulse sequences with cyclic motion encoding can encode motion on the order of hundreds of nanometers, it is contemplated that the present invention can provide highly sensitive and improved adhesion detection, thereby allowing earlier diagnosis and reducing the risk of future complications.

The present invention may also be employed to diagnose the local extracapsular invasion of prostate tumors. If a tumor is located within the capsule, the slip interface between the prostate and the periprostatic fat will be intact and a shear line should be visible in MR images acquired in accordance with the present invention while applying a vibrations to the pelvis. Extracapsular invasion would compromise the tissue interface and this shear line would not be observed. It is also contemplated that the present invention may be used for the localization of boundaries between the functional compartments of the multi-tendoned forearm muscles. This would be beneficial for the MR spectroscopy, electromyography, or biopsy studies of the forearm musculature for exercise physiological investigations and for the treatment of diseases like focal dystonia of the hand. Likewise, the focal absence of pericardial signal voids due to transepicardial tumor invasion or adhesions could be used to diagnose the pericardial involvement in cases like hepatocellular carcinoma.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:

1. A method for producing, with a magnetic resonance imaging (MRI) system, an image indicating an integrity of a tissue interface in a subject, the method comprising the steps of:
   a) applying an oscillatory stress to the subject to impart a relative shearing motion between tissues at opposing sides of a common tissue interface including a tissue slip interface;
   b) acquiring nuclear magnetic resonance (NMR) signals from a region-of-interest including the tissue slip interface with the MRI system, while applying a motion encoding gradient along the direction of the imparted relative shearing motion to sensitize the acquired NMR signals to the relative shearing motion at the tissue slip interface;
   c) reconstructing at least one magnetic resonance elastography (MRE) image from the acquired NMR signals;
   d) analyzing the at least one reconstructed MRE image to determine a loss of signal intensity due to intra-voxel phase dispersion (IVPD) resulting from the imparted relative shearing motion at the tissue slip interface; and
   e) producing, from the determined loss of signal intensity, an image indicative of the mechanical connectivity between the tissues at opposing sides of the common tissue slip interface.

2. The method as recited in claim 1 wherein step b) includes:
   b) i) acquiring a first set of NMR signals while applying the motion encoding gradient; and
   b) ii) acquiring a second set of NMR signals while applying a motion encoding gradient having a polarity opposite that of the motion encoding gradient applied in step b) i).

3. The method as recited in claim 2 wherein step c) includes:
   c) i) reconstructing a first image from the first set of NMR signals;

c) ii) reconstructing a second image from the second set of NMR signals; and c) iii) producing the at least one MRE image by determining a mean amplitude value from amplitude values at corresponding locations of the first and second images and calculating a phase difference from phase values at corresponding locations of the first and second images.

4. The method as recited in claim 3 wherein the loss of signal intensity due to intra-voxel phase dispersion is determined by:

generating a complex image with unit magnitude and phases equal to the phase differences calculated in step c) iii); and applying a low-pass filter to the complex image to discern image regions having phase discontinuities below a selected cutoff from image regions having phase discontinuities above the selected cutoff.

5. The method as recited in claim 3 wherein the loss of signal intensity due to intra-voxel phase dispersion is determined by:

calculating two-dimensional phase difference values from phase difference values calculated in step c) iii) using root-sum-of squares; and estimating a maximum observable signal loss from the calculated two-dimensional phase difference values.

6. The method as recited in claim 5 wherein the maximum observable signal loss is estimated using the relationship:

$$\frac{R^2}{N^2} = 1 - 4\alpha(1-\alpha)\sin^2\left(\frac{\Delta\theta}{2}\right)$$

in which R is a net magnitude signal of a given voxel, N is a total number of spins in the voxel, α is a fraction of spins in a compartment of the voxel, and Δθ denotes the calculated phase difference values.

7. A method of producing an image of a tissue interface in a subject using a magnetic resonance imaging (MRI) system, the method comprising the steps of:

applying an oscillatory stimulus to the subject to impart relative shearing motion between tissues at opposing sides of a common tissue interface including a tissue slip interface;

acquiring nuclear magnetic resonance (NMR) signals from a region-of-interest including the tissue slip interface, while applying a motion encoding gradient along the direction of the relative shearing motion to sensitize the acquired NMR signals to the relative shearing motion between the tissues along the tissue slip interface;

determining a loss of signal intensity due to intra-voxel phase dispersion (IVPD) resulting from the imparted relative shearing motion at the tissue slip interface; and reconstructing, from the acquired NMR signals, a magnetic resonance elastography (MRE) image indicating a degree of mechanical shear connectivity at the tissue slip interface.

8. The method as recited in claim 7 wherein acquiring NMR signals from the region-of-interest includes:

acquiring a first set of data while applying the motion encoding gradient; and acquiring a second set of data while applying a motion encoding gradient having a polarity opposite that of the motion encoding gradient applied when acquiring the first set of data.

9. The method as recited in claim 8 wherein reconstructing the MR image includes:

reconstructing a first image from the first set of data using two-dimensional Fourier transformation;

reconstructing a second image from the second set of data using two-dimensional Fourier transformation; and selectively combining the first and second images to produce the MRE image.

10. The method as recited in claim 9 wherein selectively combining the first and second images includes determining a mean amplitude value from amplitude values at corresponding locations of the first and second images and calculating a phase difference between phase values at corresponding locations of the first and second images.

11. The method as recited in claim 10 further comprising the step of processing the MR image to provide an improved depiction of the tissue slip interface.

12. The method as recited in claim 11 wherein processing the MR image includes differentiating between signal loss at the tissue slip interface due to IVPD and inherent MR image contrast between the two tissues.

13. The method as recited in claim 12 wherein differentiating between signal loss at the tissue slip interface due to IVPD and inherent MR image contrast between the two tissues includes:

generating a complex image with unit magnitude and phases equal to the calculated phase differences; and applying a low-pass filter to the complex image to discern image regions having phase discontinuities below a selected cutoff from image regions having phase discontinuities above the selected cutoff.

14. The method as recited in claim 13 wherein the low-pass filter is a nine-point Hamming windowed low-pass filter with a normalized frequency cut-off of 0.5.

15. The method as recited in claim 12 wherein differentiating between signal loss at the tissue slip interface due to IVPD and inherent MR image contrast between the two tissues includes:

calculating two-dimensional phase difference values from one-dimensional phase difference values in the MR image using root-sum-of squares; and estimating a maximum observable signal loss from the calculated two-dimensional phase difference values.

16. The method as recited in claim 15 wherein the maximum observable signal loss is estimated using the relationship:

$$\frac{R^2}{N^2} = 1 - 4\alpha(1-\alpha)\sin^2\left(\frac{\Delta\theta}{2}\right)$$

in which R is a net magnitude signal of a given voxel, N is a total number of spins in the voxel, α is a fraction of spins in a compartment of the voxel, and Δθ denotes the calculated phase difference values.

17. The method as recited in claim 8 wherein the MR image is used to assess a slip functionality of the tissue slip interface.

18. The method as recited in claim 17 wherein assessing the slip functionality of the tissue slip interface includes identifying at least one of abdominal adhesions, local extracapsular invasion of prostate tumors, and functional compartments of multitendoned forearm muscles.

19. The method as recited in claim 7 further comprising analyzing at least one of the NMR signals to identify a lack of phase discontinuities associated with the common tissue slip interface and the reconstructed MRE image to identify an absence of shear lines in the MRE image and, therefrom, identifying an abnormality associated with the common tissue slip interface.

20. A magnetic resonance imaging (MRI) system configured to produce an image indicating an integrity of a tissue interface in a subject, the system comprising:
   a magnet system configured to generate a polarizing magnetic field about at least a portion of a subject arranged in the MRI system;
   a plurality of gradient coils configured to apply a gradient field to the polarizing magnetic field;
   a radio frequency (RF) system configured to apply an excitation field to the subject and acquire MR image data therefrom;
   a driver configured to deliver an oscillatory stress to the subject;
   a computer system programmed to:
      cause the driver to deliver the oscillatory stress to the subject to impart a relative shearing motion along a direction of an imparted relative shearing motion and between tissues at opposing sides of a common tissue interface including a tissue slip interface;
      control the plurality of gradient coils to apply a motion encoding gradient along the direction of the imparted relative shearing motion;
      control the RF system to acquire nuclear magnetic resonance (NMR) signals from a region-of-interest of the subject including the tissue slip interface and sensitized to the relative shearing motion at the tissue slip interface by the motion encoding gradient;
      reconstruct a magnetic resonance elastography (MRE) image from the acquired NMR signals;
      analyze at least one of the NMR signals and the reconstructed MRE image to determine a loss of signal intensity due to intra-voxel phase dispersion (IVPD) resulting from the imparted relative shearing motion at the tissue slip interface; and
      produce, using the determined loss of signal intensity, an image indicative of the mechanical connectivity between the tissues at opposing sides of the common tissue slip interface.

* * * * *